United States Patent [19]
Boehringer et al.

[11] Patent Number: 5,992,239
[45] Date of Patent: Nov. 30, 1999

[54] GAUGE

[75] Inventors: John R. Boehringer, Wynnewood; John Karpowicz, Chester Springs; Michael I. Hegedus, Royersford, all of Pa.

[73] Assignee: Boehringer Laboratories, Inc., Norristown, Pa.

[21] Appl. No.: 09/150,184

[22] Filed: Sep. 10, 1998

[51] Int. Cl.[6] .............................. G01L 7/08; A61B 5/00
[52] U.S. Cl. ........................... 73/715; 600/485; 600/498
[58] Field of Search .............................. 73/700, 715, 716, 73/744, 146.8; 600/490, 491, 498, 485

[56] References Cited

U.S. PATENT DOCUMENTS

| | | | |
|---|---|---|---|
| 3,391,691 | 7/1968 | Young | 73/700 |
| 4,182,175 | 1/1980 | Boehringer . | |
| 4,231,375 | 11/1980 | Boehringer . | |
| 4,283,954 | 8/1981 | Echtler et al. | 73/706 |
| 4,382,739 | 5/1983 | Mack et al. | 414/217 |
| 4,552,153 | 11/1985 | Newman et al. | 128/677 |
| 4,966,035 | 10/1990 | Huang | 73/146.8 |
| 5,189,979 | 3/1993 | Popenoe | 116/273 |

*Primary Examiner*—Benjamin R. Fuller
*Assistant Examiner*—Abdullahi Aw-Musse
*Attorney, Agent, or Firm*—Paul & Paul

[57] ABSTRACT

A gauge is provided, preferably for patient use, in which a piston moves linearly within a gauge body against the force of a spring. A diaphragm separates the sensing side of the piston from the clean or atmosphere side of the piston. The diaphragm rolls against the piston and the wall of the chamber during changes in pressure, and does not interfere with accuracy of the readings. Dampening is provided out of the patient fluid stream. The sight glass through which measurements are read produces an optical magnification. A baffle prevents entrained particles from the patient from entering the gauge in significant amounts. A surface-to-surface seat enables the gauge to be mounted as a saddle seat on a duct, regulator or the like.

11 Claims, 3 Drawing Sheets

GAUGE

BACKGROUND OF THE INVENTION

In the art of gauges, particularly gauges for suction control, and most particularly in the medical field where air, other gas or fluid emanating from a patient is to be controlled, it is desirable to have a gauge that is tolerant of abuse, but which lends itself to being repeatedly taken apart, cleaned and sterilized.

Generally, dial or rotary gauges, with a pointer for rotary indication have been employed. Such gauges typically require relatively sophisticated know-how and tools for calibration, are not tolerant of abuse and are difficult or nearly impossible to clean and sterilize.

SUMMARY OF INVENTION

The present invention is directed to providing a gauge of relatively simple construction, that lends itself to continued, accurate operation even when subjected to abuse.

The present invention thus provides a gauge which employs linear movement by means of a piston movable in a conduit, with a diaphragm separating the patient side of the gauge from atmosphere, with a rolling motion of the diaphragm.

Another feature of the present invention provides a suction gauge, whereby the patient connection side is isolated from atmosphere by means of a fluid-impermeable diaphragm, and whereby dampening of the motion of the diaphragm against rapidly varying line conditions is provided, with the dampening being out of the patient fluid stream. The fluid can be air, other gases, or liquids.

It is another aspect of this invention to provide a gauge for measuring negative pressure during fluid flow of air from a patient, in which the fluid flow is produced by a suction or partial vacuum, and wherein entrained particles such as sputum or the like are deflected from the instrument by means of a baffle at the inlet side of the gauge.

It a further object of this invention to provide a gauge having indicia for measuring relative pressure, such as vacuum, and in which optical magnification of indicia readings is possible by means of a sight glass having a lens effect.

It is another object of this invention to provide a gauge adapted to be mounted on a duct, regulator or the like, by means of a surface-to-surface saddle mount.

Other objects and advantages of the present invention will be readily apparent to those skilled in the art from a reading of the following brief descriptions of the drawing figures, detailed descriptions of the preferred embodiments, and the appended claims.

BRIEF DESCRIPTION OF THE DRAWING FIGURES

FIG. 1 is a front view of the gauge of this invention, shown mounted on a fragmentally illustrated duct, regulator or the like.

DETAILED DESCRIPTION OF THE PREFERRED EMBODIMENTS

Figure 2:
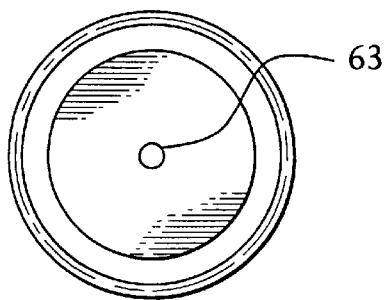
FIG. 2 is a top view of FIG. 1.
Figure 1:
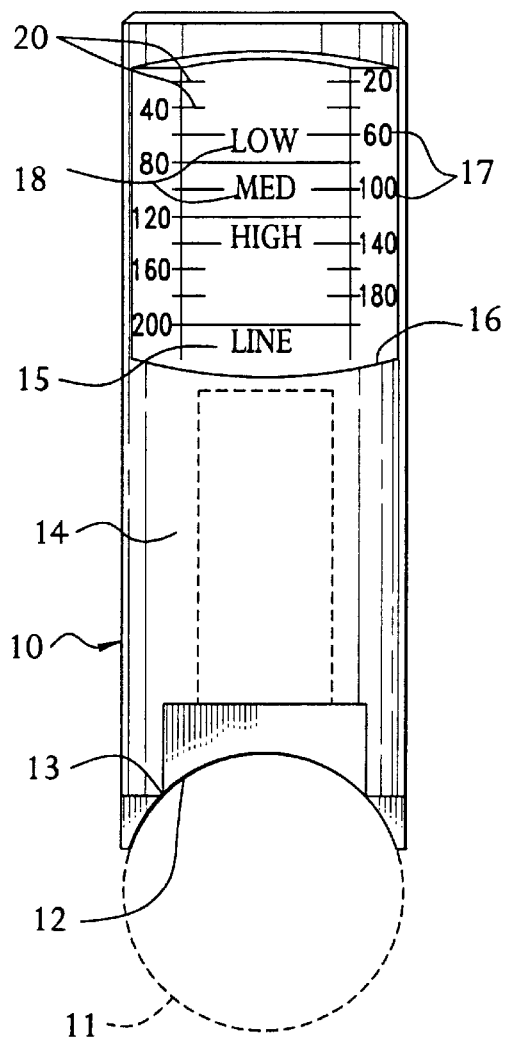
Figure 3:
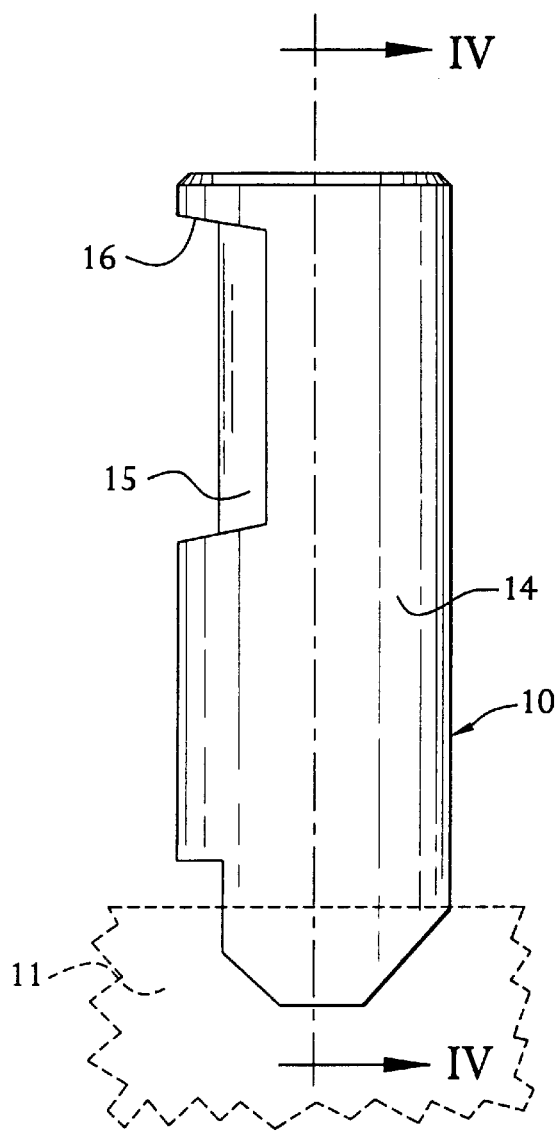
FIG. 3 is a right side view of the gauge of FIG. 1.

Referring now to the drawings in detail, reference is first made to FIG. 1, wherein the gauge 10 is being shown in surface-to-surface saddle mounted relation to a duct 11. The duct 11 is shown in phantom, and can comprise a portion of a regulator on which the gauge 10 is mounted, such as a suction regulator, or any other type of duct. The lower surface 12 of the gauge 10 is shown as being arcuate, such as being a segment of a concave, cylindrical surface, for mating with a complementally configured surface 13 of the duct 11.

The gauge 10 includes a gauge body 14, generally cylindrical in configuration, and having a sight glass 15 in a window 16 at the upper end thereof, with the sight glass having various numerical and word indicia 17 and 18, respectively. The sight glass 15 is constructed as a lens to make the numbers and words 17,18, as well as the horizontal graduations 20, appear to be larger than they actually are.

Figure 4:
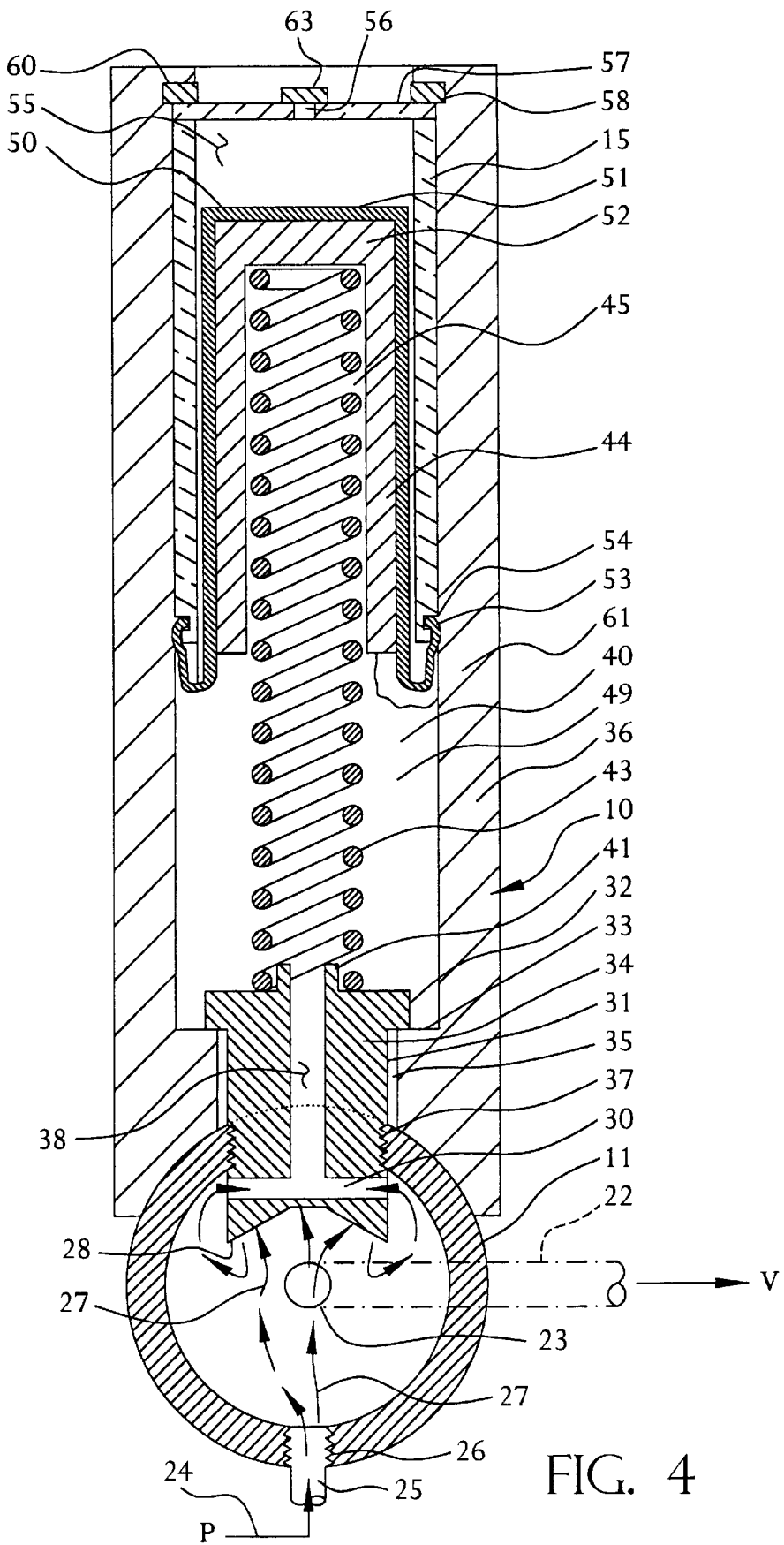
FIG. 4 is a vertical sectional view of the gauge of FIG. 3, taken generally along the line IV—IV of FIG. 3, and wherein there is shown air being received from a patient and drawn into a duct via a source of partial vacuum, with entrained particles striking a baffle, with the gauge being shown as including a vertically movable piston and diaphragm.

Referring now to FIG. 4, it will be seen that vacuum V is drawn on the duct 11 via line 22 connected to the duct 11 at inlet 23, to draw air or other gases from a patient P via line 24, shown as a pipe 25 threaded into the duct 11, as at 26.

Thus, air from the patient P is drawn into the duct 11 and moves in the direction of the arrows 27, such that any entrained particles, including liquid particles such as sputum, can strike baffle surfaces 28 and be deflected downwardly, to pass outwardly via hole 23, rather than entering the transverse opening 30 in the gauge fastener 31 at the lower end of the gauge 10. The fastener 31 includes a head 32 secured against seat 33 at its upper end, with shank 34 of the fastener 31 passing through the hole 35 at the lower end of the gauge body 36 and secured to the duct 11 in threaded engagement therewith, as shown at 37. The opening 30 communicates with a vertical bore 38 through the fastener 31 that in turn communicates with the conduit 40. An upstanding shoulder 41 is provided for the fastener 31, for placement of the lower end of a compression spring 43 in seated engagement thereabout. A piston 44 is disposed in conduit 40, for vertical linear movement upwardly and downwardly therein.

The piston 44 has a vertical bore 45 therein for receiving the upper end of the compression spring 43, as shown.

The piston 44 and conduit 40 have respective cylindrical walls 46 and 47. It will also be understood that the gauge body 36, the fastener 31, the compression spring 43, the piston 44 and the sight glass 15 are all generally cylindrical in construction.

A diaphragm 50, sleeve-like in construction, having a flat upper end 51 in engagement with the upper end 52 of the piston 44, and carried thereby, has an opposite end 53 clamped in engagement in a outer annular groove 54 at the lower end of the sight glass 48 and against an associated upper end of the wall 47 of the conduit 40, as shown in FIG. 4. The diaphragm 50 is impermeable to air or other fluids or gases, and is flexible, being constructed of a rubber-like material such as silicone or the like, and seals patient air in the conduit 40 against entry into the zone 55 at the upper end of the gauge 10, to keep patient air from passing to atmosphere via the upper opening 56 in the cover 57. The cover 57 is held in place by a washer-like snap ring 58 engaged within an annular groove 60, as shown.

Figure 5:
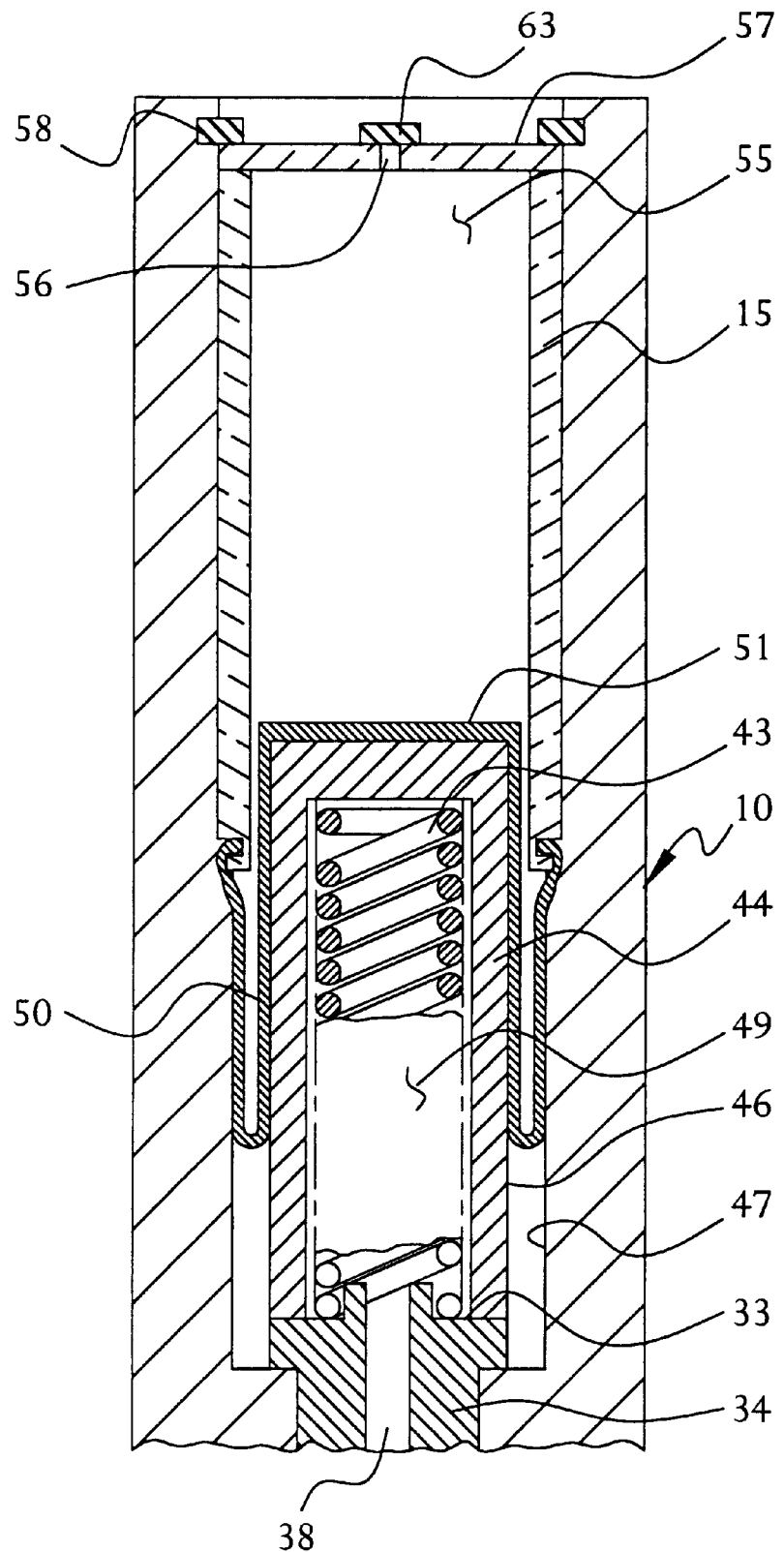
FIG. 5 is a fragmentary view of a portion of the gauge shown in FIG. 4, but wherein the vertically movable piston is shown in a fully withdrawn, or lower position, with the rolling diaphragm in rolling engagement with both the wall of the conduit in which the piston rides and with the outer wall of the piston.

As increased vacuum is drawn via line 22, the diaphragm 50 and piston 44 are drawn downwardly from the position shown in FIG. 4, to that shown in FIG. 5, with the lower end 61 of the piston seated against the head 32 of the fastener 31. As the piston moves linearly upwardly or downwardly within the bore conduit 40, the diaphragm 50 rolls along the outer cylindrical surface 46 of the piston, and also rolls along the inner cylindrical surface 47 of the gauge body 36, providing a substantially friction-free sealed engagement between zones 49 and 55, respectively on opposite sides of the diaphragm 50.

A dampening is provided against abrupt motions of the piston 44, so that visual indications of the upper end of the piston relative to graduations appearing on the sight glass are smooth. The dampening effect is provided in such a way as to do the dampening out of the patient fluid stream; namely, via upper opening 56. The opening 56 is of a cross-sectional area that is smaller than the aggregate cross-sectional entry area of opening 30. A filter 63 is also provided for the opening 56, in order keep dust or other particles from entering the zone 55, and air is drawn into the zone 55 during descent of the piston 44. As the piston moves upwardly, air within the zone 55 enters atmosphere.

The cover 57 will preferably be constructed of a generally transparent material in order to allow light to enter the zone 55, to enhance the readability of the indicia of the gauge, as the upper end of the piston moves among the various graduations of the gauge.

It will thus be seen that the gauge of this invention provides a durable instrument capable of withstand the rigors of portable instrumentation.

It will be seen that the source of vacuum V can be of any type, but will often be the general hospital vacuum source. In such medical applications, the air being drawn often aspirates potentially infectious material. The simplicity of construction of the gauge of the present invention allows repeated disassembly, cleaning and sterilization, as needed. Also, such disassembly and reassembly can be done without needing special tools or requiring complex calibration. The gauge of this invention is easy to read and provides for accurate reading. Moreover, it is tolerant of abusive conditions, will withstand variations in pressure/suction, and is capable of withstanding an environment that may include mixtures of gas and water vapor, as well as environments in which biological materials such as blood and mucus are present.

The dampening effect that is provided against rapid vibration is provided on the atmospheric or clean side of the diaphragm, allowing for unobstructed passage of air into and out of the sensing chamber below the diaphragm.

It will be apparent from the foregoing that various modifications may be made in the use and operation of the gauge of the present invention, all within the spirit and scope of the invention as defined in the appended claims.

What is claimed is:

1. A gauge for measuring relative pressure of air, other gases or other fluids relative to a patient, comprising:

(a) a gauge body having a first end adapted to be mounted on a source of fluid to be measured and a second end spaced from said first end, with said first and second ends having respective first and second fluid openings therein;

(b) the gauge body having a generally linear conduit extending between said first and second ends;

(c) a linearly movable piston in said conduit, moveable relative to said first and second ends in response to relative fluid pressure applied to a said fluid opening;

(d) a spring in said conduit, normally urging said piston toward an-extended position near one of the said ends of the gauge body in opposition to relative pressure applied at a said fluid opening;

(e) with said conduit having a conduit wall and with said piston having a piston wall and a generally transverse end, and with said walls having space therebetween, and with said walls having relative motion therebetween during linear movement of the piston;

(f) a fluid impermeable flexible diaphragm in said conduit, separating said first and second openings from fluid communication therebetween across said diaphragm; with said diaphragm being carried by said piston for linear movement of a portion of the diaphragm therewith;

(g) with a portion of the diaphragm being fixedly mounted in the conduit and sealingly separating the first and second ends from each other;

(h) with the diaphragm having surface means in rolling engagement with said wall of said conduit and in rolling engagement with said wall of said piston during linear movement of the piston in said conduit;

(i) at least a generally transparent sight portion associated with said gauge body; said piston transverse end being visible through said sight portion in response to fluid pressure applied to a fluid opening; and indicia means carried by said sight portion, for indicating relative fluid pressure at one said opening, in response to visible linear movement of said transverse end of said piston relative to said indicia means.

2. The gauge of claim 1, wherein said first opening is adapted to have partial vacuum air pressure applied thereto as the fluid, and wherein said second opening is in communication with atmospheric air, and wherein said spring is disposed for normally urging said piston toward said second end and comprising means whereby said piston's movement toward said first end in response to partial vacuum applied at said first end is resisted by the force of said spring.

3. The gauge of claim 2, wherein said second opening is of a cross-sectional area smaller than the cross-sectional area of said first opening and comprises means whereby a dampening resistance is applied to linear motion of said piston.

4. The gauge of claim 3, including filter means in said second opening for filtering particles from entering said second opening along with air.

5. The gauge of any one of claims 1–4, wherein said conduit wall, said piston wall and said diaphragm are generally cylindrical in configuration.

6. The gauge of claim 3, wherein means are provided connecting said first opening to a patient's gaseous fluid stream, whereby the diaphragm seals said first opening from the patient's gaseous fluid stream.

7. The gauge of any one of claims 1–4, said generally transparent sight portion associated with said gauge body being curved to comprise lens means in said sight portion for visually enlarging said indicia means for optically enhanced readability of an indication of relative fluid pressure.

8. The gauge of any one of claims 2, 3 or 6, including baffle means at said first end for engaging particles entrained in fluid being drawn toward said first opening by the partial vacuum, and thereby providing means whereby such particles will strike said baffle means and be deflected from said first opening.

9. The gauge of claim 1, wherein said gauge is generally cylindrical in configuration.

10. The gauge of any one of claims 1–4 or 9, wherein said first end is adapted to be connected to a duct member that is generally arcuate in exterior configuration, and wherein said first end is generally arcuate in configuration, comprising means facilitating a surface-to-surface saddle mount between said first end and a duct member to which the gauge is to be connected.

11. The gauge of claim 1, wherein said gauge body is of generally cylindrical configuration; wherein piston is of generally cylindrical configuration and is movable between first and second ends generally concentrically in said gauge body; wherein said diaphragm is of generally cylindrical configuration in the extended position of said piston.

* * * * *